(12) United States Patent
Leeflang et al.

(10) Patent No.: US 8,512,293 B2
(45) Date of Patent: Aug. 20, 2013

(54) VALVES AND HUBS FOR TUBULAR MEDICAL DEVICES AND METHODS FOR MAKING AND USING THEM

(75) Inventors: Stephen A. Leeflang, Sunnyvale, CA (US); Christian S. Eversull, Palo Alto, CA (US)

(73) Assignee: AUST Development, LLC, Palo Alto, CA (US)

( * ) Notice: Subject to any disclaimer, the term of this patent is extended or adjusted under 35 U.S.C. 154(b) by 294 days.

(21) Appl. No.: 12/856,555

(22) Filed: Aug. 13, 2010

(65) Prior Publication Data
US 2011/0040260 A1 Feb. 17, 2011

Related U.S. Application Data

(60) Provisional application No. 61/233,803, filed on Aug. 13, 2009, provisional application No. 61/233,805, filed on Aug. 13, 2009.

(51) Int. Cl.
*A61M 5/178* (2006.01)

(52) U.S. Cl.
USPC .................................................. 604/167.03

(58) Field of Classification Search
USPC ................... 604/167.01–167.04, 246, 167.03
See application file for complete search history.

(56) References Cited

U.S. PATENT DOCUMENTS

| | | |
|---|---|---|
| 4,430,081 A | 2/1984 | Timmermans |
| 4,512,766 A | 4/1985 | Vailancourt |
| 4,549,879 A | 10/1985 | Groshong |
| 4,960,412 A | 10/1990 | Fink |
| 4,973,319 A | 11/1990 | Melsky |
| 5,000,745 A | 3/1991 | Guest et al. |
| 5,125,904 A | 6/1992 | Lee |
| 5,147,332 A | 9/1992 | Moorehead |
| 5,201,901 A | 4/1993 | Harada et al. |
| 5,250,034 A | 10/1993 | Appling et al. |
| 5,267,966 A | 12/1993 | Paul |
| 5,304,143 A | 4/1994 | Green et al. |
| 5,312,355 A | 5/1994 | Lee |
| 5,441,504 A | 8/1995 | Pohndorf et al. |
| 5,453,095 A | 9/1995 | Davila et al. |
| 5,702,370 A | 12/1997 | Sylvanowicz et al. |

(Continued)

FOREIGN PATENT DOCUMENTS

| | | |
|---|---|---|
| EP | 0198962 A1 | 10/1986 |
| GB | 2284452 | 6/1995 |
| WO | 98/00195 A1 | 1/1998 |

*Primary Examiner* — Kevin C Sirmons
*Assistant Examiner* — Bradley Osinski
(74) *Attorney, Agent, or Firm* — William A. English; Vista IP Law Group LLP

(57) ABSTRACT

A hub for a sheath, catheter, or other tubular device includes a tubular hub body including first and second ends, and a lumen extending therebetween and surrounding a central longitudinal axis, the lumen having a first cross-sectional area sized for receiving a medical device therethrough. A valve is secured within the lumen that includes an elastomeric valve body including a passage extending therethrough between front and rear surfaces thereof and offset from the central axis. The valve body defines a second cross-sectional area larger than the first cross-sectional area in a relaxed state in which the passage defines an oval shape, and is secured within the lumen in a compressed state in which the passage is compressed to a closed configuration for sealing the passage from fluid flow. The passage is resiliently expandable to accommodate receiving an instrument therethrough while providing a seal around the instrument.

20 Claims, 8 Drawing Sheets

(56) References Cited

U.S. PATENT DOCUMENTS

| | | |
|---|---|---|
| 5,944,697 A | 8/1999 | Biche |
| 6,086,570 A * | 7/2000 | Aboul-Hosn et al. ........ 604/256 |
| 6,290,668 B1 | 9/2001 | Gregory et al. |
| 6,544,247 B1 | 4/2003 | Gardeski et al. |
| 6,712,791 B2 | 3/2004 | Lui et al. |
| 6,808,509 B1 | 10/2004 | Davey |
| 6,966,896 B2 | 11/2005 | Kurth et al. |
| 2001/0000041 A1 | 3/2001 | Selmon et al. |
| 2003/0050604 A1 | 3/2003 | Lui et al. |
| 2005/0192537 A1 * | 9/2005 | Osborne et al. .......... 604/167.01 |
| 2007/0293845 A1 | 12/2007 | Leeflang et al. |
| 2010/0185153 A1 * | 7/2010 | Sugiki et al. ............. 604/167.04 |
| 2011/0004223 A1 | 1/2011 | Leeflang et al. |

\* cited by examiner

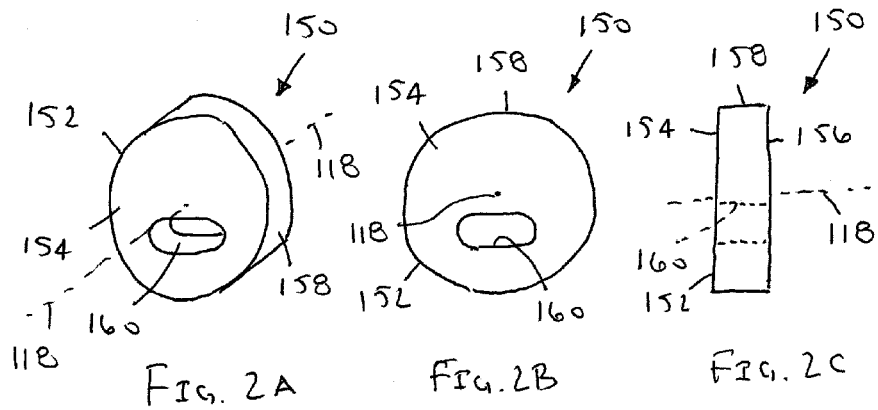
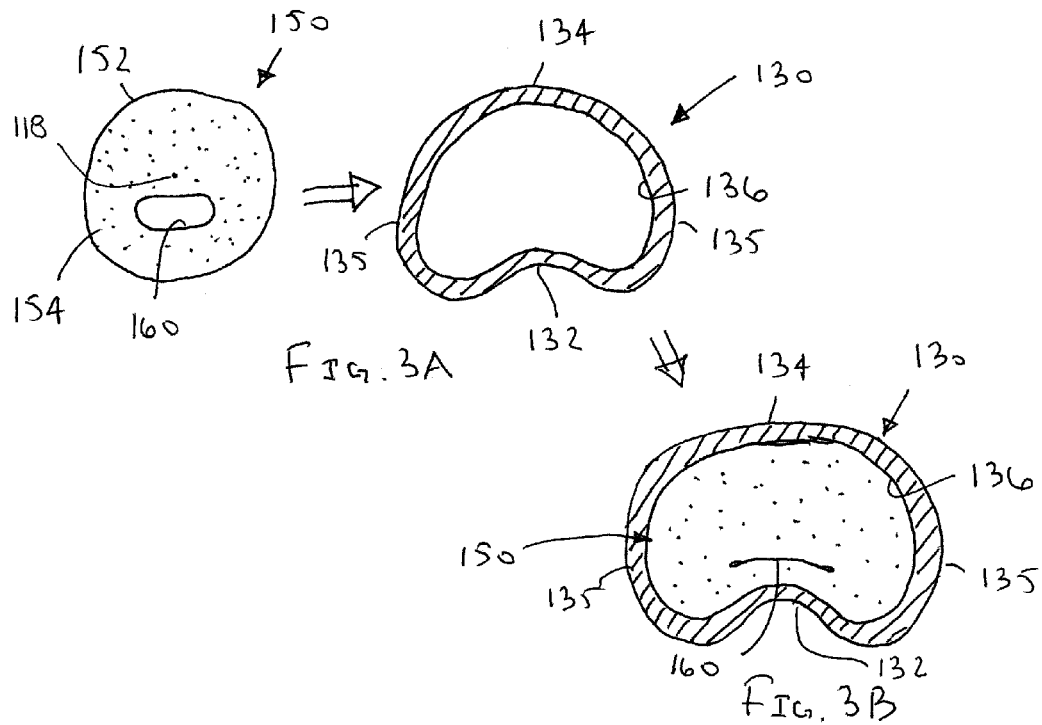

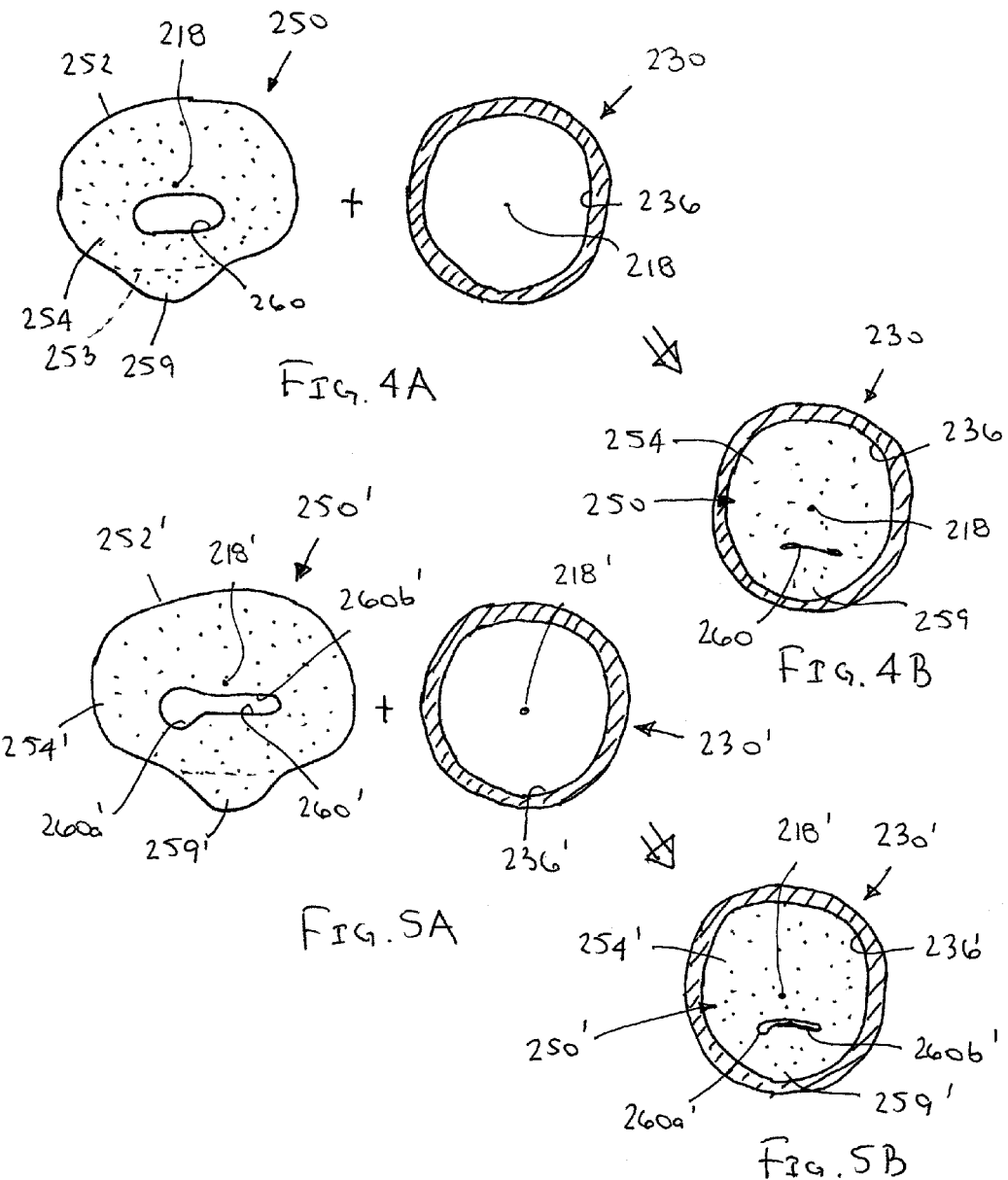

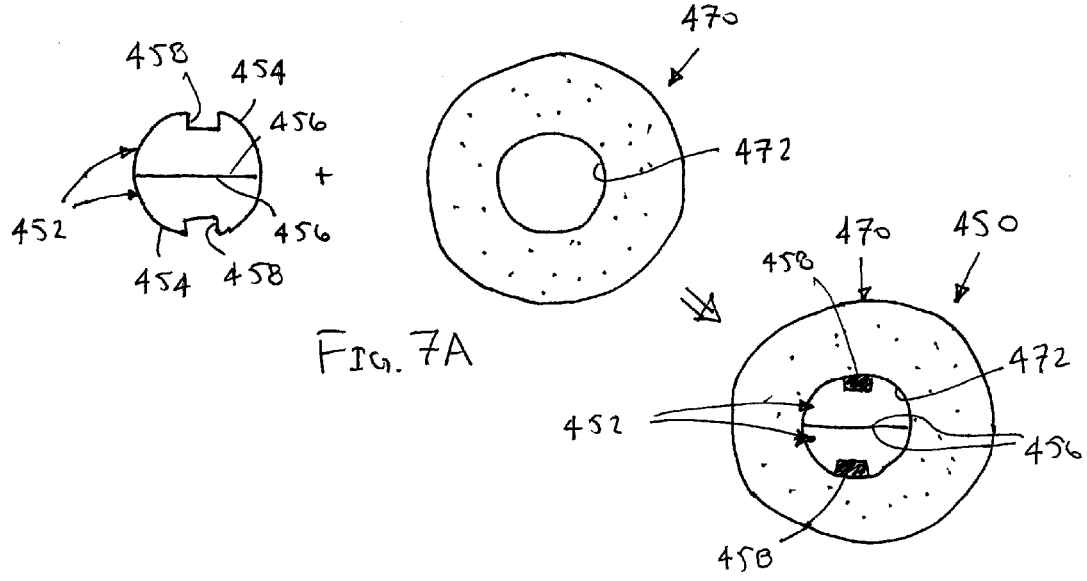
FIG. 7A
FIG. 7B
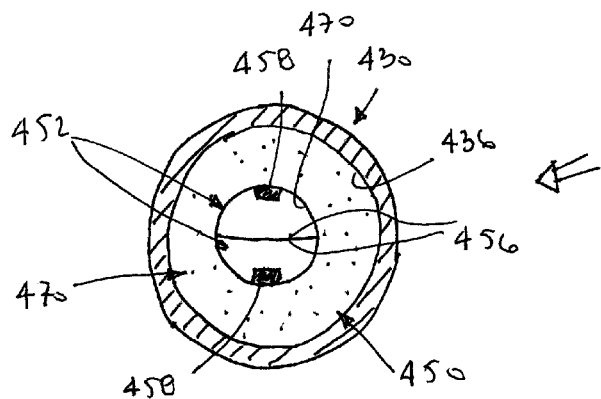
FIG. 7C

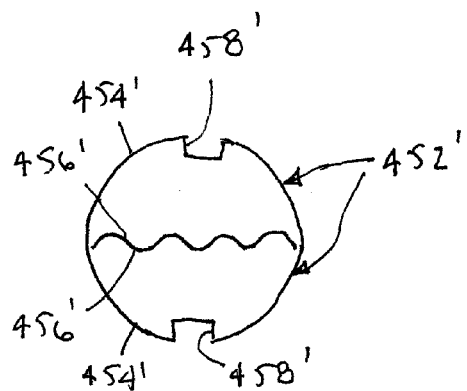
FIG. 8A
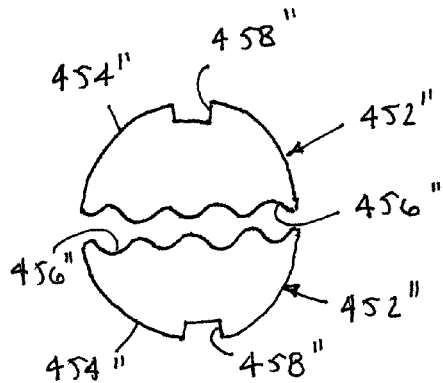
FIG. 8B
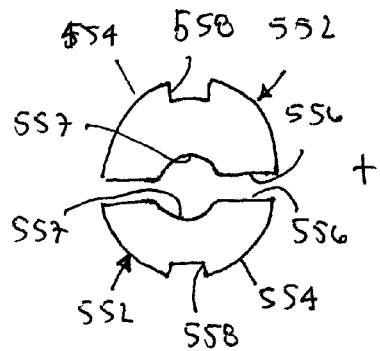 +
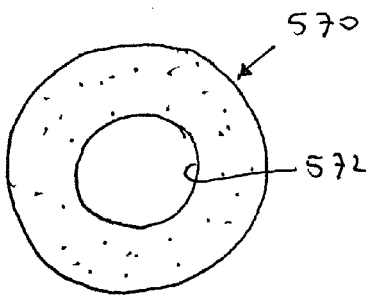
FIG. 9A
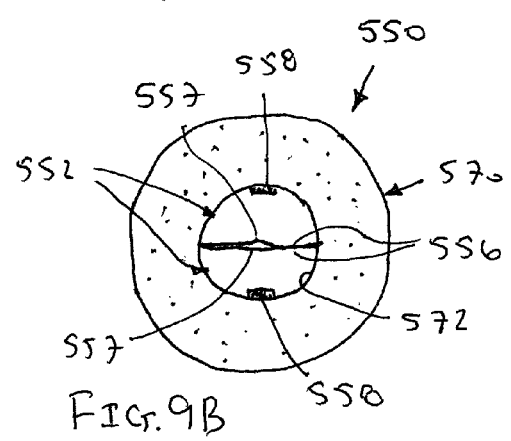
FIG. 9B

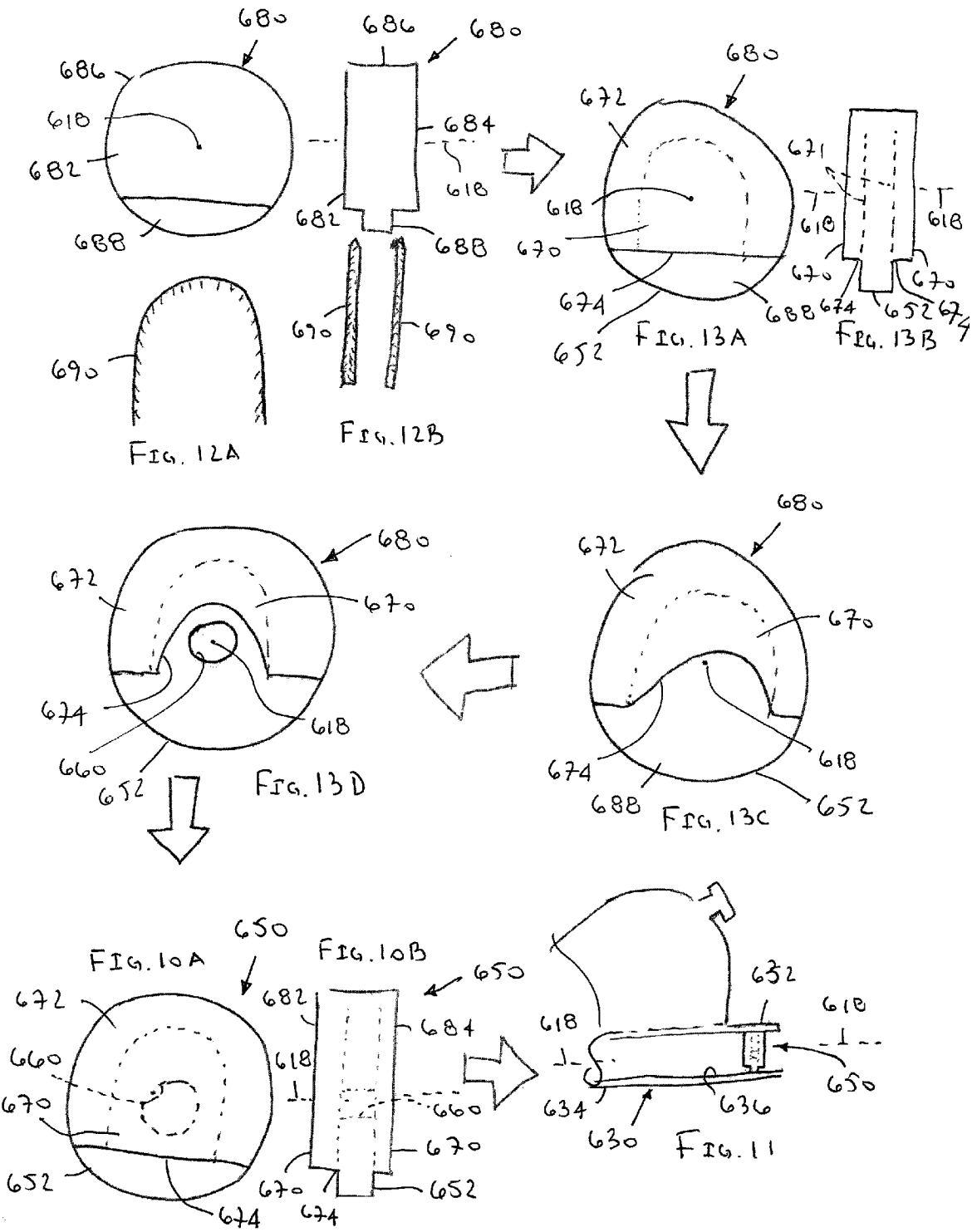

VALVES AND HUBS FOR TUBULAR MEDICAL DEVICES AND METHODS FOR MAKING AND USING THEM

This application claims benefit of provisional applications Ser. Nos. 61/233,803 and 61/233,805, both filed Aug. 13, 2009, the entire disclosures of which are expressly incorporated by reference herein.

FIELD OF THE INVENTION

The present invention relates generally to apparatus and methods for delivering instruments and/or agents during a medical procedure, and, more particularly, to valves and/or hubs for guide sheaths, catheters, and other tubular devices for accessing body lumens and/or delivering instruments into body lumens of a patient, and to methods for making and using them.

BACKGROUND

There are many medical procedures where a lead, catheter, electrode, and/or other medical device may be implanted into a patient's body cavity, recess, vessel, organ, and/or other body lumen. In many of these procedures, a delivery sheath, guide catheter, or other tubular member may be used to facilitate delivering the medical device, with the tubular member removed after placement of the medical device. Additionally, it may be desirable to provide a substantially fluid tight seal between the delivery sheath, guide catheter, or other tubular member and the lead, catheter, electrode, guidewire, and/or other medical device, e.g., for the purpose of hemostasis, infusion of therapeutic or diagnostic agents, and the like. However, the process of removing the tubular member from around the medical device after the medical device has been placed may be difficult and/or time consuming.

For example, a delivery sheath used to deliver a cardiac lead may not be easily removed from around the lead without disturbing the placement of the lead, which must remain in the patient. Therefore, an apparatus that may facilitate the delivery of devices, provide a seal or substantial seal, and/or facilitate removal without substantially disturbing placement of the lead and/or other device may be desirable.

SUMMARY

The present invention is directed generally to apparatus and methods for delivering instruments and/or agents during a medical procedure. More particularly, the present invention is related to valves and/or hubs for guide sheaths, catheters, and other tubular devices for accessing and/or delivering instruments into body lumens of a patient, and to methods for making and using them.

In accordance with one embodiment, a hub is provided for a sheath, catheter, or other tubular device that includes a tubular body including a first end, a second end, and a lumen extending therebetween and surrounding a central longitudinal axis, the lumen having a first cross-sectional area sized for receiving a medical device therethrough. A valve is secured within the lumen that includes an elastomeric valve body including front and rear surfaces extending across the lumen and a passage extending through the valve body between the front and rear surfaces and offset from the central axis. The valve body may define a second cross-sectional area larger than the first cross-sectional area in a relaxed state and/or the passage may define an oval shape in the relaxed state. The valve may be secured within the lumen in a compressed state in which the passage is biased to a closed configuration for substantially sealing the passage from fluid flow therethrough, the passage resiliently expandable to accommodate receiving an instrument therethrough while providing a substantially fluid tight seal around the instrument.

In one embodiment, the valve body may include a substantially circular disk shape in the relaxed state, and the hub may include an eccentric shape for imposing a radially inward force on the valve body for biasing the passage to the closed configuration. For example, the hub may define a kidney shape including a concave wall region opposite a convex wall region, and the valve may be secured within the lumen such that the passage is disposed between the central axis and the concave wall region. The curvature of the concave wall region may apply a radially inward force towards the passage for biasing the passage to the closed configuration.

In another embodiment, the hub may define a substantially circular cross-section, the valve body may include an eccentric shape in the relaxed state, and the valve body may be secured within the lumen in a compressed state that imposes a radially inward force on the valve body for biasing the passage to the closed configuration. For example, the valve body may include a radial portion extending radially outwardly adjacent the passage. The radial portion may be compressed radially inwardly when the valve is secured within the tubular body, thereby biasing the passage to the closed configuration.

In yet another embodiment, an insert may be embedded in the valve body radially inwardly from the passage, e.g., along the central axis, the insert applying a radially outward force between the valve body and the hub, thereby biasing the passage to the closed configuration.

In accordance with another embodiment, a hub is provided for a sheath, catheter, or other tubular device that includes a tubular body including a first end, a second end, and a substantially circular lumen extending therebetween and surrounding a central longitudinal axis, the lumen having a first cross-sectional area sized for receiving a medical device therethrough. A valve may be secured within the lumen that includes a resilient valve body having a noncircular shape in a relaxed state defining a second cross-sectional area larger than the first cross-sectional area. For example, the valve body may include front and rear surfaces extending across the lumen, and a passage extending through the valve body between the front and rear surfaces and offset from the central axis, the passage defining an oval shape in the relaxed state. The valve may be secured within the lumen in a compressed state in which the passage is compressed to a closed configuration for substantially sealing the passage from fluid flow therethrough, the passage resiliently expandable to accommodate receiving an instrument therethrough while providing a substantially fluid tight seal around the instrument.

In accordance with still another embodiment, a method is provided for making a hub for a sheath, catheter, or other tubular device. A tubular body may be provided that includes a first end, a second end, and a lumen extending therebetween and surrounding a central longitudinal axis, the lumen having a first cross-sectional area sized for receiving a medical device therethrough. A valve body may be formed from resilient material, e.g., silicone or other elastomeric material, the valve body including a front surface, a rear surface, a perimeter surface extending between the front and rear surfaces, and a passage extending through the valve body between the front and rear surfaces and offset from the central axis. The valve body may define a second cross-sectional area larger than the first cross-sectional area, e.g., in a relaxed state free from external forces, and the passage may define an oval shape in the relaxed state.

The valve body may be compressed such that the cross-sectional area of the valve body is smaller than the first cross-sectional area, e.g., such that the passage is compressed to a closed configuration, and the compressed valve body may be inserted into the lumen of the tubular body. After the compressed valve body is positioned and/or oriented within the lumen as desired, the valve body may be released within the lumen such that the valve body is constrained in a compressed state within the hub and the passage is biased to a closed configuration for substantially sealing the passage from fluid flow therethrough. Optionally, the valve body may be attached to the hub, e.g., by one or more connectors, bonding with adhesive, welding, fusing, and the like. The resulting hub may include a valve with a passage that is resiliently expandable to accommodate receiving an instrument therethrough while providing a substantially fluid tight seal around the instrument.

In accordance with yet another embodiment, a method is provided for making a valve for a sheath, catheter, or other tubular device that includes a hub including a first end, a second end, and a lumen extending therebetween and surrounding a central longitudinal axis. A valve body may be formed from resilient material including a front surface, a rear surface, a perimeter surface extending between the front and rear surfaces, and a passage extending through the valve body between the front and rear surfaces and offset from the central axis, the passage defining an oval shape. For example, the valve body may be molded or otherwise formed with the passage therethrough. Alternatively, the valve body may formed as a solid body and the passage may be created through the solid body, e.g., by stamping, mechanically cutting, machining, coring, laser cutting, and the like.

A slit may be formed through the valve body between the front and rear surfaces, the slit located radially inwardly from the passage, e.g., intersecting the central axis. An insert may be secured within the slit to open the slit and apply a compressive force, e.g., radially outwardly, on the passage to bias the passage to a closed configuration, thereby providing a valve with a passage biased to the closed configuration yet resiliently expandable to accommodate introducing one or more instruments therethrough.

Optionally, the resulting valve may be secured within the lumen of a hub or other tubular body such that the passage is biased to the closed configuration for substantially sealing the lumen from fluid flow therethrough, the passage resiliently expandable to accommodate receiving an instrument through the lumen while providing a substantially fluid tight seal around the instrument.

In accordance with still another embodiment, a valve is provided for a hub of a sheath, catheter, or other tubular device that includes a valve body including a front surface, a rear surface, and a pocket extending through the valve body from the front surface to the rear surface, the pocket defining a first diameter. A pair of valve elements may be secured within the pocket, the valve elements including peripheral surfaces engaging the valve body and slit surfaces contacting one another to provide a slit between the slit surfaces. The valve elements may define a second diameter larger than the first diameter in a relaxed state and may be resiliently compressible such that the valve elements are secured in the pocket in a compressed state. The slit surfaces may be biased against one another in the compressed state to maintain the slit substantially sealed, yet separable, e.g., when an instrument is inserted between the slit surfaces, to create a passage that accommodates the instrument while providing a substantial seal around the instrument.

In accordance with yet another embodiment, a method is provided for making a valve for a sheath, catheter, or other tubular device that includes forming or otherwise providing a valve body including a front surface, a rear surface, and a pocket extending through the valve body from the front surface to the rear surface, the pocket defining a first diameter. A pair of valve elements may also be formed or otherwise provided, each valve element including a peripheral surface defining a portion of a circle having a second diameter larger than the first diameter in a relaxed state and a slit surface, the slit surfaces of the valve elements contacting one another to provide a slit between the slit surfaces. The valve elements may be compressed radially inwardly, and the compressed valve elements may be positioned and/or released within the pocket. The valve elements may be constrained by the valve body in a compressed state. For example, the slit surfaces may be biased against one another in the compressed state to maintain the slit substantially sealed, yet separable when an instrument is inserted between the slit surfaces to accommodate the instrument while providing a substantial seal around the instrument.

In accordance with still another embodiment, a valve is provided that includes an integrally formed solid body of elastomeric material including a front surface, a rear surface, a peripheral surface extending between the front and rear surfaces, and a central axis extending through the front and rear surfaces. The solid body may partially separated to create a central body region and a pair of flaps or membranes on opposite sides of the central body region. The central body region may include a passage extending therethrough substantially parallel to the central axis. A front flap may include a peripheral region coupled to the central body portion and an open end created by partially separating the front surface of the solid body from the central body region, and a rear flap may include a peripheral region coupled to the central body portion opposite the front flap and an open end created by partially separating the rear surface of the solid body from the central body region. The front and rear flaps may cover opposite openings of the passage in a relaxed state to substantially seal the passage, and the front and rear flaps may be resiliently movable to expose the respective openings of the passage to accommodate directing an instrument through the passage.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 2A-2C are perspective, front, and side views, respectively, of an exemplary embodiment of a valve that may be coupled to the hub of FIGS. 1A and 1B.

FIG. 3A is a front view of the valve of FIGS. 2A-2C and a cross-sectional view of an exemplary embodiment of a hub, and FIG. 3B shows the valve secured in the hub.

FIG. 4A is a front view of another exemplary embodiment of a valve and a cross-sectional view of another embodiment of a hub, and FIG. 4B shows the valve secured in the hub.

FIG. 5A is a front view of an alternative embodiment of a valve and a cross-sectional view of the hub of FIGS. 4A and 4B, and FIG. 5B shows the valve secured in the hub.

FIG. 7A is a front view of a pair of valve elements and a valve body including a pocket for receiving the valve elements.

FIG. 7B is a front view of the valve elements secured in the valve body of FIG. 7A to provide a valve and showing a cross-sectional view of a hub for receiving the valve.

FIG. 7C shows the valve secured in the hub of FIG. 7B.

FIGS. 8A and 8B are front views of alternative embodiments of valve elements that may be included in the valve and hub of FIGS. 7A-7C.

FIG. 9A is a front view of yet another embodiment of valve elements that may be secured within a valve body, and FIG. 9B is a front view of a valve formed by securing the valve elements in the valve body of FIG. 9A.

FIGS. 10A and 10B are front and side views, respectively, of another embodiment of a valve including a pair of release flaps covering a passage through a central body of the valve.

FIG. 11 is a cross-sectional detail of a hub including the valve of FIGS. 10A and 10B secured therein.

FIGS. 12A and 12B are front and side views, respectively, of a valve body showing blades forming release flaps from front and rear surfaces of the valve body.

FIGS. 13A and 13B are front and side views, respectively, of the valve body of FIGS. 12A and 12B after forming the release flaps.

FIGS. 13C and 13D are front views of the valve body of FIGS. 13A and 13B, showing a method for forming a passage through a central body of the valve body to provide the valve of FIGS. 10A and 10B.

DETAILED DESCRIPTION OF THE EXEMPLARY EMBODIMENTS

Figure 1A:
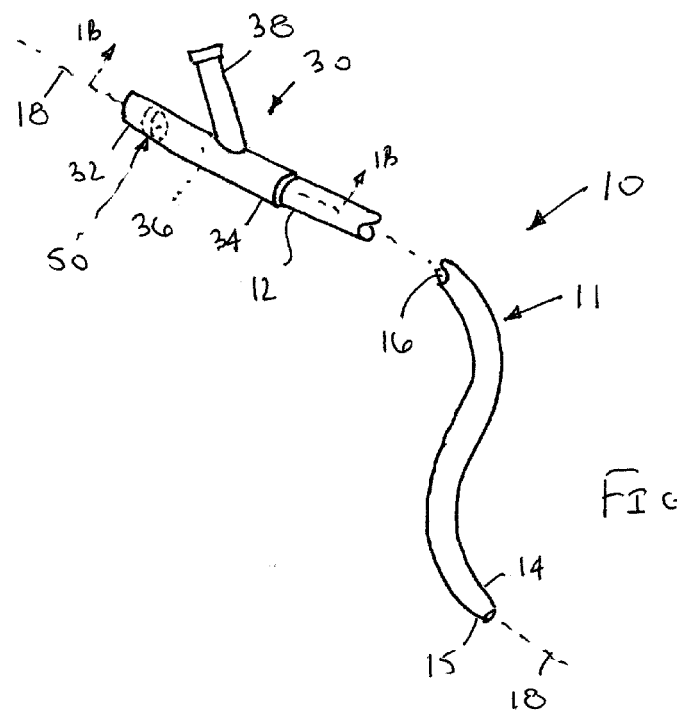
FIG. 1A is a perspective view of an exemplary embodiment of a tubular device, including a hub on its proximal end and a valve connectable to the hub.
Figure 1B:
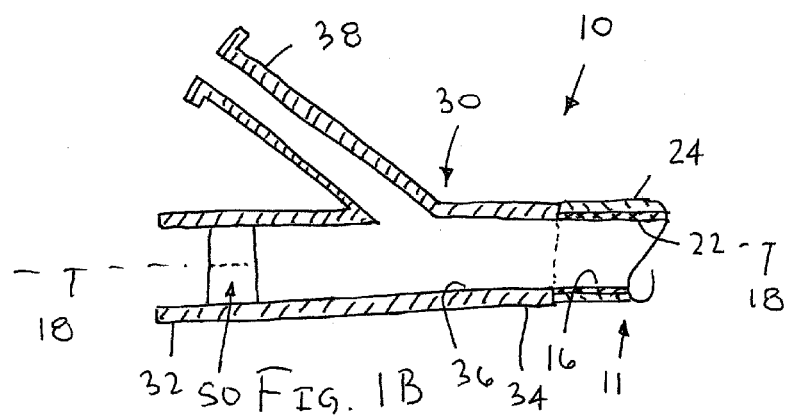
FIG. 1B is a cross-sectional view of the proximal end of the tubular device of FIG. 1A, taken along line 1B-1B.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 includes an elongate tubular body 11 including a proximal end 12, a distal end 14 sized for introduction into a body lumen, a lumen 16 extending between the proximal and distal ends 12, 14 along a central longitudinal axis 18, and a handle or hub 30 on the proximal end 12 including a valve 50 for allowing one or more devices to be introduced into the lumen 16. The hub 30 and/or valve 50 may include any of the embodiments described elsewhere herein. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other instrument (not shown), and/or for delivering fluids or other flowable agents or materials therethrough, as described further below.

As can be seen in FIG. 1B, the tubular body 11 may be constructed from one or more layers, e.g., an inner liner 22 surrounding the lumen 16, a reinforcing layer surrounding the inner liner (not shown), and an outer layer 24. Optionally, one or more coatings (not shown) may be applied to the inner surface of the inner liner 22. In an exemplary embodiment, a hydrophilic coating, such as Polyvinylpyrrolidone, may be sprayed or otherwise applied onto the surface of the inner liner 22 during fabrication to provide a lubricious inner surface for the lumen 16 of the tubular body 11. Exemplary materials and methods for making the tubular body 11 are disclosed in co-pending application Ser. No. 11/340,904, filed Jan. 26, 2006, Ser. No. 11/670,958, filed Feb. 2, 2007, Ser. No. 12/254,818, filed Oct. 20, 2008, and Ser. No. 12/551,540, filed Aug. 31, 2009. The entire disclosures of these references are expressly incorporated by reference herein.

The layers of the tubular body 11 may be attached to one another, e.g., by laminating, adhering, adhesive bonding, ultrasonic welding, reflowing or other heating, and the like. The construction of the tubular body 11 may be substantially uniform or may vary between the proximal and distal ends 12, 14, e.g., by varying the inner liner, 22, reinforcing layer, and/or outer layer 24 along the length of the tubular body 11. Optionally, the inner liner 22, reinforcing layer, and/or outer layer 24 may include one or more sublayers (not shown), which may vary in construction in various portions of the tubular body 11.

In one exemplary embodiment, the proximal end 12 may be substantially rigid or semi-rigid, e.g., providing sufficient column strength to allow the tubular body 11 to be pushed from the proximal end 12, while the distal end 14 may be substantially flexible or semi-rigid. Thus, the distal end 14 of the tubular body 11 may be advanced or otherwise manipulated within a patient's body from the hub 30 and/or proximal end 12 without substantial risk of buckling and/or kinking.

In exemplary embodiments, the tubular body 11 may have an outer diameter between about half and twenty millimeters (0.5-20 mm) or between about one and five millimeters (1-5 mm), and a length between about five and one hundred fifty centimeters (5-150 cm). The inner liner 22 may have a wall thickness between about 0.0001-0.01 inch (0.0025-0.25 mm) and the outer layer 24 may have a wall thickness between about 0.0005-0.2 inch (0.0127-5.08 mm).

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to facilitate the apparatus 10 being pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another. Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970. The entire disclosures of these references are expressly incorporated by reference herein.

Optionally, the distal end 14 may include a tapered, rounded, or otherwise shaped distal tip 15, e.g., to provide a substantially atraumatic tip and/or to facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Returning to FIG. 1B, an exemplary embodiment of a hub 30 is shown that includes a main tubular hub portion including a first end 32, a second end 34 coupled to the proximal end 12 of the 32b, and a lumen 36 extending therebetween. The hub 30 may include one or more side ports, e.g., a first side port 38 communicating with the lumen 16. Optionally, one or more additional side ports (not shown) may be provided on the hub 30 communicating with respective lumen(s), e.g., if the tubular body 11 includes an inflation lumen for a balloon on the distal end 14 (also not shown) and/or other lumen. The side port 38 may include a connector (not shown), for example, a luer lock connector, a hemostatic seal, and the like, e.g., for coupling a source of fluid, inflation media, and/or vacuum (not shown) to the side port 38.

The hub 30 may have a substantially uniform wall thickness, or, alternatively, the thickness may vary around a circumference of the hub 30. For example, the hub 30 may include a relatively thin or weakened region (not shown) extending axially along the hub 30, e.g., to facilitate slitting the hub 30 during use. In an exemplary embodiment, the relatively thin region may be disposed generally opposite the side port 38, e.g., such that the relatively thin region may be slit without substantial interference from the side port 38.

Optionally, the hub 30 may include one or more other connectors, e.g., luer lock connectors, electrical connectors, and the like (not shown), for connecting other devices (not shown) to the apparatus 10, such as syringes, displays, controllers, and the like (also not shown). In addition, the hub 30 may include one or more actuators, such as sliders, buttons, switches, and the like, e.g., for activating and/or manipulating components (also not shown) on the distal end 14 or otherwise operating the apparatus 10.

Components of the hub 30 may be integrally formed together as a single piece or may be formed separately and then attached together to provide the hub 30. For example, the main hub portion and side port 38 may be formed as a single piece, e.g., by injection molding, casting, and the like. Alternatively, the main hub portion and side port 38 may be formed separately, e.g., by extrusion, injection molding, casting, and the like, and attached together as desired, e.g., using cooperating connectors (not shown), bonding with adhesive, fusing, sonic welding, heat bonding, reflowing, insert molding, and the like. The hub 30, side port 38, and/or any other components may be formed from plastic, metal, or composite materials, as desired, such as nylon, PEBAX, PTFE, HDPE, and the like.

Turning to FIGS. 2A-2C, an exemplary embodiment of a valve 150 is shown that includes a valve body 152, e.g., generally having a disc shape including a front surface 154, a rear surface 156, and a perimeter surface 158 extending between the front and rear surfaces 154, 156. As shown, the valve 150 has a generally circular disk shape, e.g., with the front and rear surfaces 154, 156 defining a diameter of the valve body 152 in a relaxed state, and the perimeter surface 158 defining a thickness of the valve body 152. A bore or other passage 160 extends through the valve body 152 between the first and second surfaces 154, 156, e.g., for receiving one or more instruments therethrough, as described elsewhere herein.

The valve 150 may be formed from elastomeric material, such as silicone, chronoprene, isoprene, santoprene, and the like. Thus, as described further below, the valve body 152 may be resiliently compressible from the relaxed state to a compressed state, e.g., to facilitate securing the valve 150 within a hub and/or sealing the passage 160 while allowing the passage 160 to resiliently open to accommodate receiving one or more devices therethrough. In one embodiment, the valve body 152 may be integrally formed as a single piece including the passage 160, e.g., by injection molding, casting, and the like. Alternatively, the valve body 152 may be formed as a solid body and the passage 160 may be formed into the solid body, e.g., by mechanically cutting, machining, stamping, coring, laser cutting, and the like.

The valve body 152 may be formed such that both the perimeter surface 156 and/or the passage 160 extend substantially parallel to a central longitudinal axis 118 (which may correspond to the axis 18 of the apparatus 10 shown in FIGS. 1A and 1B) when the valve 150 is secured within a hub, such as hub 130 shown in FIGS. 3A and 3B. The passage 160 may be offset laterally from the central axis 118, e.g., such that the passage 160 is closer to the perimeter surface 160 of the valve body 152 on one side than the opposite side. Thus, a region of the valve body 52 adjacent the bore 62 may be thinner on one side of the valve body 52 than other surrounding regions, which may facilitate slitting the valve 50 during use, as explained further below.

As shown, the passage 160 has an oval shape, e.g., including a relatively larger width or major axis and a relatively smaller height or minor axis orthogonal to the major axis, with the minor axis extending radially inwardly towards the central axis 118. As used herein, "oval" includes a continuously curved elliptical shape, an elongate curved shape, i.e., including substantially straight parallel opposing walls connected by curved walls, an elongate eye shape, or any other elongated curved shape including rounded and/or abrupt edges or corners.

The passage 160 may be sized appropriately to allow an instrument (not shown) to pass freely through the passage 160 without substantial frictional resistance and/or to provide a seal around the medical device to prevent substantial fluid leakage when the medical device is passed through the passage 160. For example, the perimeter of the passage 160 may be at least slightly smaller than the circumference of any instruments to be inserted through the passage 160. Optionally, the valve body 152 may be resiliently flexible such that the passage 160 may be dilated or otherwise expanded when an instrument is inserted through the passage 160 and may resiliently return to its original size when the instrument is removed. Thus, the passage 160 may expand to accommodate a medical device having a larger cross-section than the passage 160 in a relaxed, unexpanded but open configuration. For example, with the passage 160 in the relaxed configuration (e.g., without a medical device inserted therethrough), the passage 160 may have an effective diameter (perimeter/n given its oval shape) between about 0.25 and eight millimeters (0.25-8 mm), but may be expandable to larger diameters, e.g., between about 0.35 and ten millimeters (0.35-10 mm).

Optionally, the valve 150 (or any of the other embodiments herein) may include one or more additional features. For example, at least the front surface 154 may be tapered inwardly towards the rear surface 156 (not shown), e.g., to facilitate introduction of an instrument into the passage 160. In addition or alternatively, the valve body 152 may include one or more connectors or other features (not shown) to facilitate attaching or otherwise securing the valve 150 within a hub (also not shown). Optionally, lubricant or other material may be introduced into the passage 160, e.g., into one or more recesses (not shown) in a wall of the passage 160, if desired, to facilitate inserting one or more instruments and/or otherwise reducing friction through the passage 160.

Turning to FIGS. 3A and 3B, the valve 150 may be secured in a hub 130, which may be provided for the hub 30 of the apparatus 10 shown in FIGS. 1A and 1B, e.g., to provide a sheath, catheter, or other tubular member. The valve 150 may accommodate receiving one or more instruments, e.g., a catheter, lead, guidewire or other medical device (not shown), through the hub 130 and into the lumen 16 of the tubular body 11, while providing a substantially fluid-tight seal to prevent substantial fluid leakage from the lumen 16.

As shown in FIGS. 3A and 3B, the hub 130 may have an eccentric or noncircular cross-section along at least a portion of its length, i.e., the portion within which the valve 150 is secured. For example, the hub 130 may have a circumferential wall having a "kidney" shaped cross-section, i.e., defining a concave lower wall region 132 opposite a convex upper wall region 134. Thus, the lumen 136 of the hub 130 may have a noncircular, e.g., kidney, shape, as shown, with the upper and lower wall regions 132, 134 closer to one another than opposite side wall regions 135 of the hub 130 connecting the upper and lower wall regions 132, 134 to one another.

The cross-sectional area of the lumen 136 may be at least slightly smaller than the surface area of the valve 150, e.g., of the front surface 154, such that the valve body 152 needs to be compressed radially inwardly before the valve 150 may be inserted and/or secured in the lumen 136 of the hub 130. For example, as shown in FIG. 3B, the valve body 152 may be oriented such that the passage 160 is closest to the lower concave surface 132 of the hub 130 (i.e., with the major axis of the passage 160 directed towards the side wall regions 135), and the valve body 152 may be compressed inwardly sufficient to introduce the valve body 152 into the lumen 136 of the hub 130. Once the valve body 152 is positioned at a desired location within the hub 130 (e.g., adjacent the proximal end 32 as shown in FIGS. 1A and 1B), the valve body 152 may be released within the lumen 136. Because the valve body 152 is compressed, the valve body 152 may resiliently try to expand back towards its relaxed state, but such expansion may be limited by the walls of the hub 130 given the smaller cross-sectional area available. Thus, the hub 130 may constrain the valve body 152 and impose a radially inward force that biases the passage 160 to a closed configuration, as shown in FIG. 3B, which may provide a substantially fluid-tight seal when no instruments are introduced through the valve 150.

Optionally, the hub 130 and/or valve body 152 (or any of the other valves and/or hubs herein) may include one or more alignment features (not shown) to ensure that the valve 150 is properly oriented when oriented within the lumen 136. For example, one of the hub 130 and the valve body 152 may include one or more tabs (not shown) that may be received in corresponding one or more slots (also not shown) in the other of the hub 130 and the valve body 152 only when the valve 150 is oriented properly relative to the hub 130.

The hub 130 may be substantially rigid, e.g., such that the shape of the hub 130 does not change to accommodate receiving the valve 150 therein. Alternatively, the hub 130 may be semi-rigid, e.g., such that the shape of the hub 130 may change slightly when the valve 150 is released within the hub 130 to distribute forces while still constraining the valve 150 sufficiently to bias the passage 160 to the closed configuration.

The resulting interference fit from the valve 150 trying to resiliently expand may be sufficient to secure the valve 150 within the hub 130. In addition or alternatively, the valve 150 may be secured to the hub 130 using other methods, e.g., at least one of bonding with adhesive, welding, fusing, one or more connectors, (not shown), and the like. Where adhesive is used to secure the valve 150 within the hub 130 (or any of the other valves and/or hubs herein), the valve body 152 and/or the hub 130 may include recesses, channels, or other features (not shown) designed to receive and/or distribute adhesive at the interface between the hub 130 and the valve body 152.

Optionally, the hub 130 (or any of the hubs herein) may include one or more relatively thin and/or weakened regions, e.g., extending along a length of the hub 130, as described above. For example, at least a portion of the lower concave wall region 132 may have a thickness less than the side wall regions 135 and/or upper convex wall region 134. Thus, a slitter tool may be used to cut the hub 130 along the lower concave wall region 132 and the valve 150 may provide a relatively thin region for the slitter to cut through when the slitter passes through the valve 150.

With additional reference to FIGS. 1A and 1B, during use, the apparatus 10 (with the hub 130 and valve 150 of FIGS. 2A-3B) may be used for delivering a medical device into a body lumen within a patient's body, e.g., a lead, catheter, and the like, into a patient's vasculature or other body lumen, as described above. For example, a distal end 14 of the tubular body 11 may be introduced into a patient's vasculature with the hub 130 and valve 150 remaining outside the patient's body. The tubular body 11 may be advanced through the patient's vasculature, e.g., to position the distal end 14 and a desired location, e.g., a coronary vein within the patient's heart or other body lumen.

A medical device, e.g., a pacing or other electrical lead (not shown), may be inserted into the proximal end of the hub 130, through the passage 160 of the valve 150, and into the tubular body 11 until a distal end of the medical device is advanced into the body lumen, e.g., exiting or remaining within the distal end 14 of the tubular body 11. The passage 160 may resiliently expand as necessary to accommodate the medical device passing through the valve 150. If the medical device is removed and/or exchanged, the passage 160 may resiliently return to its closed configuration, as shown in FIG. 3B, thereby preventing substantial leakage of fluid from the lumen 16 out the proximal end 32 of the hub 130.

Once the medical device is positioned at a desired location, the apparatus 10 may then be removed to leave the medical device implanted within the patient's body. The configuration of the hub 130 may facilitate removing the apparatus 10 from around the medical device without substantial risk of dislodging or otherwise moving the medical device. For example, cardiac leads often include relatively large proximal hubs, e.g., including electrical connectors and the like, which may prevent the apparatus 10 from being removed over the hub. Instead, a slitter or other tool (not shown) may be used to slit the hub 130, valve 150, and tubular body 11 to open the apparatus 10 and allow easy removal despite a large hub or other obstacle.

For example, a slitter may be used to cut along the lower wall region 132 of the hub 132, as shown in FIG. 3B, until the slitter encounters the valve 150. The slitter may continue to cut through the valve 150, which may facilitated because of the relatively small thickness of material of the valve body 152 between the lower wall region 132 and the passage 160. If the hub 130 includes a relatively thin walled region, the region may be identified, e.g., by a colored line, a recess (not shown) in the proximal end 32 of the hub 130 and/or elsewhere, to facilitate identification by the user. Optionally, the tubular body 11 may include a tear-away or other weakened region that may be aligned with the relatively thin walled regions of the hub 130, which may facilitate slitting or may simply propagate separation of the region along the length of the tubular body 11 with or without use of a slitter or other tool. Alternatively, the valve 150 may include two or more parts, e.g., a pair of semi-circular or otherwise shaped portions (not shown), with at least one of the portions intersecting the passage 160 in at least one location, such that once the tubular body 11 is torn away, slit, or otherwise removed, the apparatus 10 may be removed from around the valve 150 without cutting or tearing of the valve 150.

One advantage of the valve 150 is that the valve body 152 may have an overall length that is substantially shorter than conventional valves. Unlike other valves, which may include sequential features that seal a hub alternatively with and without an instrument introduced therethrough, a single feature, i.e., the passage 160, may provide a seal during both conditions. This relatively short length may also reduce friction between the valve 150 and medical device inserted through the passage 160 since there is less surface area to contact the medical device. This is particularly useful when the valve body 52 is formed from materials, such as silicone, which may be tacky. In addition, the valve 150 may be relatively simple and/or less expensive to manufacture since the valve 150 includes only a single valve element.

Another advantage of the valve 150 is that the passage 160 may include a perimeter sufficient to allow passage of a relatively large instrument therethrough with no or relatively little elongation in the path length of the perimeter of the passage 160. By comparison, a conventional valve may rely solely on elongation of the perimeter of a passage to accommodate relatively large devices. Further, the passage 160 may be adapted to seal effectively on both relatively small and relatively large instruments, for example, by compression of the passage 160. In addition, the passage 160 may be shaped to fully seal when externally or internally compressed. Further, the passage 160 may be shaped to minimize risk of tearing when an instrument is passed through the passage 160, e.g., the passage 160 may not have any acute angles, slits, or other features that may be susceptible to tear propagation.

Turning to FIGS. 4A and 4B, another embodiment of a valve 250 is shown including a valve body 252 that may be constructed similar to the previous embodiment, e.g., generally having a disc shape including a front surface 254, a rear surface (not shown), and a perimeter surface 258. A bore or other passage 260, e.g., having an oval shape, extends through the valve body 152 between the front surface 254 and the rear surface, e.g., for receiving one or more instruments therethrough, also similar to the previous embodiment. Unlike the previous embodiment, the valve 250 has an eccentric disk shape, e.g., defining an elliptical or other noncircular shape. Thus, the valve 250 may be secured within a substantially circular hub 230 in a compressed state with the eccentric shape biasing the passage 260 to a closed configuration, as shown in FIG. 4B and described further below.

As shown, the passage 260 may be laterally offset from a central axis 218 of the valve body 252, e.g., such that the passage 260 is closer to the perimeter surface 260 of the valve body 252 on one side than the opposite side. The passage 260 has an oval shape, e.g., including a relatively larger width or major axis and a relatively smaller height or minor axis orthogonal to the major axis, with the minor axis oriented radially inwardly towards the central axis 218, similar to the previous embodiment.

To provide an eccentric valve 250, the valve body 252 may have an elliptical or other noncircular shape. For example, as best seen in FIG. 4A, the valve body 252 may define an ellipse, as demonstrated by dashed line 253, that includes an additional radial portion or protrusion 259, e.g., at a location closest to the passage 260, integrally formed as part of the valve body 252. The radial portion 259 may be compressed radially inwardly to direct the passage 260 towards the closed configuration, e.g., when the valve 250 is secured within a hub 230, as shown in FIG. 4B, and described further below.

The valve 250 may be secured within a hub 230 generally similar to the previous embodiment. For example, the hub 230 may include a lumen 236 having a cross-sectional area at least slightly smaller than the surface area, e.g., of the front surface 254, of the valve 250, such that the valve body 252 needs to be compressed before the valve 250 may be inserted and/or secured in the lumen 236 of the hub 230.

Unlike the previous embodiment, however, the hub 230 may have a substantially circular cross-section. Optionally, the hub 230 may include a relatively thin or weakened region at a desired location on its circumference that extends axially along the hub 230, e.g., to facilitate slitting, as described above. In this option, the relatively thin region may be identified to facilitate orientation of the valve 250, similar to the previous embodiment, e.g., to ensure that the passage 260 is close to the relatively thin region.

As shown in FIG. 4B, the valve body 252 may be compressed inwardly sufficient to introduce the valve 250 into the lumen 236 of the hub 230. Once the valve body 252 is positioned and/or oriented at a desired location within the hub 230 (e.g., adjacent the proximal end 32 of the hub 30, as shown in FIGS. 1A and 1B), the valve body 252 may be released within the lumen 236. Because the valve body 252 is compressed, e.g., with the radial portion 259 compressed inwardly to close the passage 260, the valve body 252 may resiliently try to expand back towards its relaxed state, with such expansion limited by the walls of the hub 230, similar to the previous embodiment. Thus, the hub 230 may constrain the valve body 252 and impose a compressive force, e.g., radially inwardly, that biases the passage 260 to the closed configuration, as shown in FIG. 4B.

The resulting interference fit from the valve 250 may be sufficient to secure the valve 250 within the hub 230. In addition or alternatively, the valve 250 may be secured to the hub 230 using other methods, e.g., at least one of bonding with adhesive, welding, fusing, one or more connectors, (not shown), and the like, similar to the previous embodiment.

During use, the passage 260 may be biased to the closed configuration by the compressive force, e.g., while an apparatus including the valve 250 and hub 230 is introduced into a patient's body. When desired, a medical device may be inserted into a proximal end of the hub 230, and through the passage 260 of the valve 250, the passage 260 resiliently expanding as necessary to accommodate the medical device passing through the valve 250. If the medical device is removed and/or exchanged, the passage 260 may resiliently return to its closed configuration, as shown in FIG. 4B.

Optionally, as shown in FIG. 5A, a valve 250' (which may be any of the valves herein) may include a passage 260' having an oval shape that includes a relatively large region 260a,' at one end of the passage 260,' and a relatively narrow region 260b.' For example, the enlarged region 260a' may have a diameter corresponding to a relatively small diameter instrument that may be introduced through the valve 250,' such as a guidewire and the like (not shown), e.g., less than about 0.014 inch, while the narrow region 260b' may define a perimeter that allows expansion of the entire passage 260' to larger diameters to accommodate relatively large diameter instruments, similar to the passages in the other valves described herein.

When the valve 250' is compressed and secured within a hub 230,' as shown in FIG. 5B, the passage 260' may be biased to a closed configuration, similar to the previous embodiments, thereby providing a substantially fluid-tight seal through the valve 250.' Because of the relatively large size of the large region 260a' in the relaxed state shown in FIG. 5A, however, the compressive forces may be lower around the large region 260a' as compared with the narrow region 260b.' Thus, when a relatively small instrument is introduced into the hub 230,' the instrument may find the path of least resistance, i.e., the large region 260a' of the passage 260' that opens easiest to accommodate receiving the instrument therethrough. The narrow region 260b' may remain substantially closed and sealed, thereby reducing the risk of leakage through the valve 250.' When a larger instrument is introduced into the hub 230,' the entire passage 260' may open as necessary to accommodate the instrument while providing a substantially fluid tight seal around the instrument.

Figure 6A:
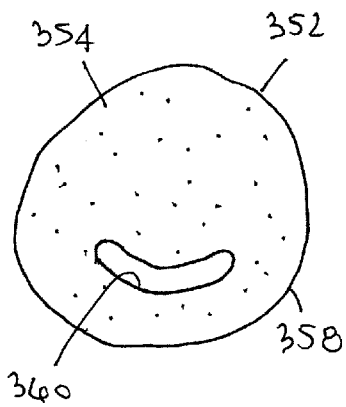
FIG. 6A is a front view of a disk body for making a valve.
Figure 6B:
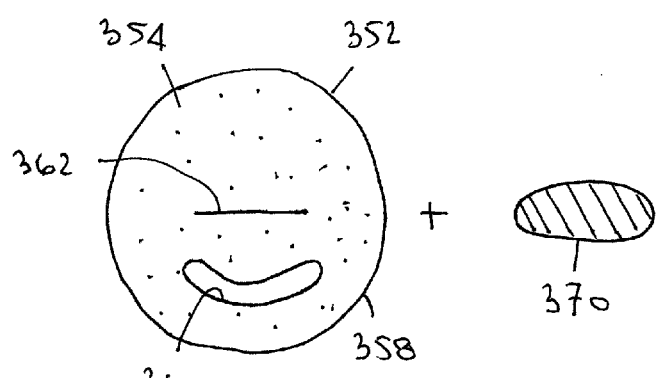
FIG. 6B is a front view of the disk body of FIG. 6A including a slit formed therethrough and a front view of an insert that may be secured in the slit.
Figure 6C:
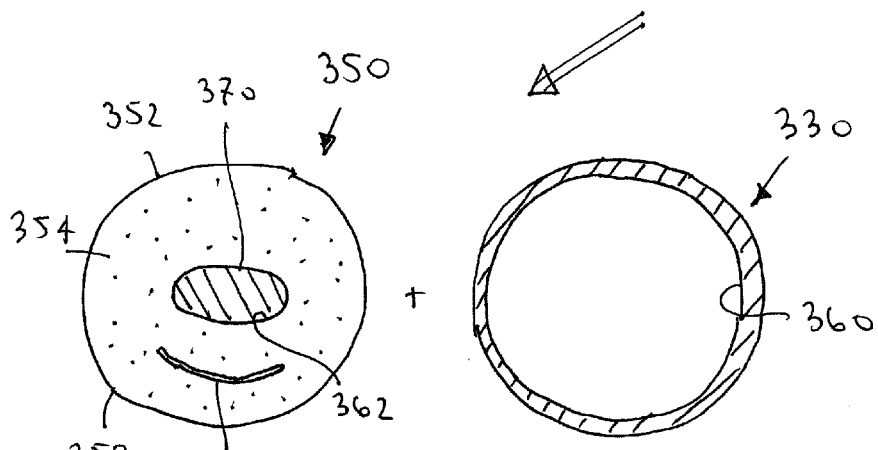
FIG. 6C is a front view of the disk body of FIG. 6B after the insert is secured in the slit to provide a valve and a cross-sectional view a hub for receiving the valve.

Turning to FIGS. 6A-6C, another method is shown for making an offset valve, i.e., a valve 350 including a bore or passage 360 therethrough that is offset laterally from a central axis 318 and is resiliently biased to a closed configuration. Initially, as shown in FIG. 6A, a valve body 352 may be formed, e.g., from elastomeric or other resiliently compressible material, similar to the previous embodiments. As shown, the valve body 352 may include a front surface 354, a rear surface (not shown), a perimeter surface 356, and a passage 360 extending between the front surface 354 and rear surface. For example, the valve body 352 may be molded, cast, or otherwise formed with the passage 360 already formed therein. Alternatively, the valve body 352 may be formed as a solid body and the passage 360 may be created through the valve body 352, e.g., by mechanically cutting, machining, stamping, coring, laser cutting, and the like.

Turning to FIG. 6B, a slit 362 may be formed through the valve body 352, e.g., extending from the front surface 354 to the rear surface. The slit 362 may be located radially inwardly from the passage 360, i.e., between the passage 360 and the central axis 318. For example, the slit 362 may intersect the central axis 318 and extend generally parallel to a major axis of the passage 362 such that the slit 362 extends transversely adjacent the passage 362 and respective ends of the slit 362 and passage 360 are spaced apart from one another a similar distance. As shown in FIG. 6B, an offset, spacer, or other insert 370 may be provided having a length similar to the length of the slit 362 and having a desired width, e.g., having an elliptical or other oval shape.

Turning to FIG. 6C, the insert 370 may be secured within the slit 362 to expand the slit 362 and/or otherwise apply a compressive force, e.g., radially outwardly, on the valve body 352 towards the passage 360 to bias the passage 360 to a closed configuration, as shown. For example, the slit 362 may be expanded and the insert 370 inserted into the expanded slit 362 to constrain the slit 362 in the expanded configuration. The insert 370 may be secured within the slit 362, e.g., by an interference fit due to the bias of the valve body 352 to close the slit 362, and/or by bonding with adhesive, sonic welding, fusing, and the like. The resulting valve 350 may include a curved oval passage 360 that is biased to a closed configuration to substantially seal the passage 360 yet resiliently expandable to accommodate receiving one or more instruments (not shown) therethrough while providing a substantial seal around the instrument(s), similar to the previous embodiments.

Figure 6D:
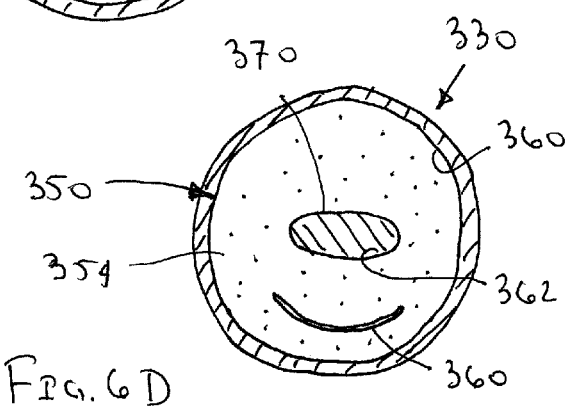
FIG. 6D shows the valve secured in the hub of FIG. 6C.

Optionally, as shown in FIGS. 6C and 6D, the valve 350 may be secured within a hub 330, similar to the previous embodiments. The valve 350 may have a cross-sectional area similar to a lumen 336 of the hub 330, e.g., such that the valve body 352 does not need to be compressed before inserting the valve 350 into the lumen 336. Alternatively, the valve 350 may have a cross-sectional area at least somewhat larger than the lumen 336, such that the valve body 352 needs to be compressed radially inwardly before inserting the valve 350 into the hub 330. The valve 350 may be attached or otherwise secured within the hub 330, e.g., by interference fit, bonding with adhesive, sonic welding, fusing, one or more connectors (not shown), and the like, similar to the previous embodiments.

Turning to FIGS. 7A and 7B, another exemplary embodiment of a valve 450 is shown that generally includes a pair of valve elements or inserts 452 and a valve body 470 for receiving the valve elements 452. The valve body 470 may be a substantially circular disk body including a pocket or aperture therethrough for receiving the valve elements 452. The valve body 470 may have an outer diameter similar to a lumen 436 of a hub 430 within which the valve 450 is secured, as shown in FIGS. 7B and 7C. Optionally, the outer diameter of the valve body 470 may be at least slightly larger than the diameter of the lumen 436, e.g., such that the valve body 470 is under compression when secured within the hub 320, similar to other embodiments herein.

Each valve element 452 may have a generally semi-circular shape defining an outer perimeter surface 454 and a substantially straight slit surface 456. The slit surfaces 456 of the valve elements 452 are oriented towards and may contact one another when the valve elements 452 are secured in the valve body 470, to provide a passage that is biased to a closed configuration, yet may be resiliently opened to accommodate introducing one or more instruments (not shown) therethrough.

For example, the valve elements 452 may have an outer diameter that is at least slightly larger than the inner diameter of the pocket 472 in the valve body 470. In exemplary embodiments, the inner diameter of the pocket 472 may be between about 0.05 and ten millimeters (0.05-10.0 mm). Thus, the valve elements 452 may be compressed radially inwardly before being inserted into the pocket 472 and then released such that valve elements 452 are constrained in a compressed state within the pocket 472. In the compressed state, the valve elements 452 may apply a compressive force, e.g., radially inwardly, on the slit surfaces 456, thereby biasing the slit surfaces 456 towards or against one another to define the closed configuration. The slit surfaces 456 may be resiliently separable to provide a passage (not shown)

between the valve elements 452, e.g., to accommodate introducing one or more instruments (also not shown) through the valve 450 while providing a substantially fluid tight seal around the instruments, similar to other embodiments herein.

The valve body 470 may have a thickness sufficient to support the valve elements 452 within the pocket 472, e.g., between about 0.05 and ten millimeters (0.05-10.0 mm). The valve elements 452 may have a thickness similar to or slightly less than the valve body 470, e.g., such that the valve elements 452 may be flush or recessed within the pocket 472. The valve body 470 and valve elements 452 may be formed from silicone or other elastomeric material to provide a resilient compressible and/or expandable valve 450, similar to other embodiments herein.

The valve elements 452 may be formed together as a single body, e.g., by molding, casting, cutting, stamping, and the like, and then separated to create the slit surfaces 456, as shown in FIG. 7A. Alternatively, the valve elements 452 may be formed separately and placed in contact with one another, e.g., being loaded into the valve body 470. Similarly, the valve body 470 may be formed as a single piece, e.g., by molding, casting, cutting, stamping, and the like, including the pocket 472. Alternatively, the valve body 470 may be formed as a solid body, and the pocket 472 created therethrough, e.g., by mechanical cutting, stamping, coring, laser cutting, and the like.

In a further alternative, the valve body 470 may be formed as separate "C" shaped elements (not shown) that may be placed together, e.g., within the hub 430, and/or attached together, e.g., by bonding with adhesive, sonic welding, fusing, and the like, to define the pocket 472. In this alternative, the seams of the valve body 470 may be offset from the orientation of the slit surfaces 456, e.g., by ninety degrees (90°). One of the advantages of this alternative is that the seams of the valve body 470 and slit surfaces 456 may be offset from one another such that a tear that is created in one of the components does not propagate to the other components but is limited by the interface between the valve body 470 and valve elements 452.

Turning to FIG. 7B, once the valve elements 452 and valve body 570 are formed, the valve elements 452 may be secured within the pocket 472 to create the valve 450. For example, as described above, the valve elements 452 may be compressed radially inwardly, inserted into the pocket 472, and released therein. The bias of the valve elements 452 to expand may provide an interference fit substantially securing the valve elements 452 within the valve body 470. In addition or alternatively, the valve elements 452 may be attached to the valve body 470, e.g., by bonding with adhesive, sonic welding, fusing, one or more connectors (not shown), and the like. For example, as shown, the valve elements 452 may include one or more channels 458, e.g., generally opposite the slit surfaces 456, for receiving an adhesive or other material to secure the valve elements 452 within the valve body 470.

The resulting valve 450 shown in FIG. 7B may be secured within a hub 430, e.g., similar to other embodiments herein, as shown in FIG. 7C. For example, the valve body 470 may be compressed radially inwardly and inserted into the lumen 436 of the hub 430 and positioned and/or oriented at a desired location. The valve body 470 may then be released within and/or attached to the hub 430, similar to the previous embodiments.

During use, when a relatively small instrument is introduced into the hub 430, the instrument may separate the slit surfaces 456 to open the passage and allow the instrument to pass through the valve 450. The slit surfaces 456 may contact the instrument and thereby provide a substantially fluid tight seal around the instrument. If an instrument is introduced into the hub 430 that is larger than the pocket 472 of the valve body 470, the slit surfaces 456 may separate and then the valve body 470 itself may resiliently expand to dilate the pocket 472 and accommodate the instrument, while providing a substantially fluid tight seal around the instrument.

One advantage of the valve 450 is that the valve elements 452 may limit the risk of a tear propagating through and creating a leak the entire valve 450. One of the risks of silicone or other elastomeric materials is that if a tear is created, the tear may propagate under relatively low stresses. For example, if the valve 450 were formed with the valve elements and valve body as a single piece with a slit therein (not shown), there would be substantial risk of the slit tearing and propagating outwardly to the outer edge of the valve body 470. However, with the valve body 470 provided as a separate component than the valve elements 452, the slit surfaces 456 provide an opening that is resistant to tearing due to the interface between the valve elements 452 and the surrounding valve body 470. Stated differently, the separate valve body 470 substantially reduces the risk of the passage defined by the slit surfaces 456 tearing to the outer edge of the valve 450.

Turning to FIG. 8A, an alternative embodiment of valve elements 452' that may be secured within a valve body, such as the valve body 470 of FIGS. 7A-7C. Unlike the previous embodiments, the valve elements 452' include generally sinusoidal slit surfaces 456' that contact one another. As shown, the slit surfaces 456' have substantially constant amplitude and period waves, although the shape of the slit surfaces 456' may be varied, if desired. In this embodiment, the slit surfaces 456' are in phase with one another, which may allow the valve elements 452' to be formed from a single body and separated by cutting or otherwise creating the slit surfaces 456.'

Alternatively, as shown in FIG. 8B, valve elements 452" may be provided that include slit surfaces 456" that are out of phase with one another. For example, as shown the slit surfaces 456" have generally sinusoidal shapes that are one hundred eighty degrees (180°) out of phase. The valve elements 452" may be sufficiently compressed together when secured within a valve body (such as the valve body 470 of FIGS. 7A-7C) that the slit surfaces 456" are compressed to a closed configuration that provides a substantially fluid tight seal between the slit surfaces 456." Because the compressive forces may be lower where the low regions of the sinusoidal slit surfaces 456" contact one another, a relatively small instrument introduced into the valve 450 may find the path of least resistance that opens easiest, i.e., between one of the opposing pairs of low regions, to accommodate receiving the instrument therethrough. Thus, a small opening between a single opposing low regions of the slit surfaces 456" may open, while the remaining regions of the slit surfaces 456" remain compressed together, thereby reducing the risk of leakage through the valve 450 by such a relatively small instrument.

Turning to FIGS. 9A and 9B, another alternative embodiment of a valve 550 is shown that includes a pair of valve elements 552 secured within a valve body 570, which may be made using materials and methods similar to the previous embodiments. For example, each valve element 552 may include a generally semi-circular shape defining an outer perimeter surface 554, slit surfaces 556, and optionally adhesive channels 558, similar to the previous embodiments. Unlike the previous embodiments, each valve element 552 may include a recess 557 in an otherwise substantially straight slit surface 556, as best seen in FIG. 9A. Thus, in a relaxed state, the opposing slit surfaces 556 may be disposed in contact with one another, other than the regions defining the recesses 557. The recesses 557 may define a predetermined diameter in the relaxed state, e.g., at least slightly smaller than a relatively small instrument that may be introduced through the valve 550, such as a 0.014 inch guidewire.

The valve body 570 may include a pocket 572 defining an inner diameter that is at least slightly smaller than the outer diameter defined by the valve elements 552. Thus, when the valve elements 522 are compressed and loaded into the pocket 572 of the valve body 570, the valve elements 522 may be subjected to a compressive force, e.g., radially inwardly, such that the slit surfaces 556 are compressed together sufficiently to provide a substantially fluid tight seal, as shown in FIG. 9B. However, similar to the valve elements 452,", the opposing recesses 557 may be subjected to lower compressive forces than other regions of the slit surfaces 556. Therefore, the surfaces defining the recesses 557 may more easily separate, e.g., to open only the portion of the passage between the recesses 557, when a relatively small instrument is introduced through the valve 550, while the rest of the passage between the slit surfaces 556 may remain substantially sealed. If an instrument is introduced through the valve 550 that is substantially larger than the diameter of the recesses 557, the entire slit surfaces 556 may separate and/or the valve body 570 may dilate, if necessary, to accommodate receiving the instrument therethrough while providing a substantially fluid tight seal around the instrument, similar to the previous embodiments.

Turning to FIGS. 10A and 10B, another embodiment of a valve 650 is shown that includes a central body region 652 including a passage 660 therethrough and a pair of release flaps or membranes 670 overlying the passage 660. The flaps 670 may include a peripheral region 672 coupled to the central body region 652 and an open end 674 for exposing and/or accessing the passage 660. For example, the flaps 670 may be biased to cover the passage 660 to provide a substantially fluid tight seal across the valve 650, e.g., when no instruments are inserted therethrough, yet may be resiliently flexible such that the flaps 670 may be stretched or otherwise directed out of the way to expose and/or access the passage 660, e.g., as shown in FIG. 13D.

Optionally, if desired, only a single release flap (not shown) may be provided on one side of the central body region 652 and the other release flap may be eliminated such that the passage 660 is exposed and/or accessible from the side without a release flap. However, one of the advantages of including both release flaps 670 is that the passage 660 may be substantially sealed whether exposed to positive or negative pressures across the valve 650, as described further below.

As shown in FIG. 11, the valve 650 may be attached or otherwise secured within or across a lumen 636 of a hub 630, similar to other embodiments herein. For example, the valve 650 may have an outer diameter at least slightly larger than the diameter of the lumen 636, e.g., such that the valve 650 may be compressed radially inwardly to allow insertion into the hub 630 and/or positioning at a desired location within the lumen 636. Alternatively, the valve 650 may have an outer diameter similar to the lumen 636 such that the valve 650 may be inserted into the hub 630 without compressing the valve 650, e.g., by sliding the valve 650 into the lumen 636. The valve 650 may be attached to the hub 630 within the lumen 636 similar to the previous embodiments, e.g., by an interference fit, bonding with adhesive, sonic welding, fusing, one or more connectors (not shown), and the like, to provide a substantially fluid tight seal between the valve 650 and the surrounding wall of the hub 630.

With continued reference to FIGS. 10A and 10B, the valve 650 may be integrally formed as a single body, e.g., from silicone or other elastomeric material, similar to the previous embodiments, with the release flaps 670 integrally formed with the central body region 652. For example, FIGS. 12A-13D show an exemplary method for making the valve 650 from a solid body 680. As shown in FIGS. 12A and 12B, the solid body 680 may have a circular or other disk shape including a front surface 682, a rear surface 684, a perimeter surface 686 extending therebetween, and defining a central longitudinal axis 618. The solid body 680 may include a relatively narrow region 688 offset laterally and axially from the front and rear surfaces 682, 684, as best seen in FIG. 12B.

To create the release flaps 670, one or more blades or other cutting tools 690 may be used to cut into the solid body 680, e.g., substantially perpendicular to the central axis 618, and adjacent the narrow region 688. The cutting tool(s) 690 may create a pocket 671 extending from an open end 674 between the release flaps 670 and the central body region 652 and at least partially surrounded by material defining the peripheral region 672 of the flaps 670. The cutting tools 690 may include one or more tools that may be used to create the pockets 671 and flaps simultaneously, as shown in FIG. 12B, or sequentially (e.g., if only one cutting is used). Exemplary cutting tools 690 that may be used include sharpened blades that mechanically cut into the solid body 680, heated blades or dies that may melt or otherwise reflow the solid body 680 to create the pocket 671, and the like.

Turning to FIGS. 13A and 13B, the cutting tool(s) 690 have been removed, after creating the pockets 671 and flaps 670. The flaps 670 may have a thickness such that the flaps 670 are sufficiently flexible and/or resilient such that the open end 674 may be stretched or otherwise directed to expose the central body region 652 surrounding the central axis 618, as shown in FIG. 13C. As shown in FIG. 13D, the passage 660 may then be created through the central body region 652, e.g., concentric with the central axis 618, for example, by mechanical cutting, laser cutting, stamping, coring, and the like. Alternatively, if desired, the passage 660 may be offset from the central axis 618, e.g., towards the narrow region 688 of the solid body 680, if it is desirable to facilitate accessing the passage 660 or away from the narrow region 688 if it is desirable to enhance sealing the passage 660 with the flaps 670.

Once the passage 660 is formed, the flaps 670 may be released, the flaps 670 resiliently returning to cover the passage 660, as shown in FIGS. 10A and 10B. With both a front and rear flap 670 covering the passage 660, a substantially fluid tight seal may be maintained when no instrument is introduced through the passage 660 even if the valve 650 is subjected to positive or negative pressure across the passage 660. For example, if the pressure is higher adjacent the front surface 682 of the valve 650 than the rear surface 684, the rear flap 670 may tend to be pulled away from the passage 660. This could create a risk of leakage from the passage 660, except that the same pressure may tend to press the front flap 670 against the central body region 652, thereby enhancing a seal over the passage 660. The opposite is true if the pressure is higher adjacent the rear surface 684 than the front surface 682.

During use, with additional reference to FIG. 11, an instrument (not shown), may be inserted into the hub 630 to introduce the instrument through the valve 650 and into the lumen 636, e.g., into a tubular body, such as tubular body 11 shown in FIGS. 1A and 1B. When the instrument contacts the front flap 670 adjacent the first end 632 of the hub, the instrument may stretch the flap 670, or otherwise resiliently direct the flap 670 out of the way such that the instrument may enter and pass through the passage 660. The rear flap 670 may simply be pushed away from the passage 660 as the instrument exits the passage 660 and enters the lumen 632 beyond the valve 650. The central body region 652 may resiliently dilate to expand the passage 660 and accommodate the instrument passing therethrough while providing a substantially fluid tight seal around the instrument. If the instrument is removed, the flaps 670 may resiliently return to their original position over the passage 660, thereby substantially sealing the passage 660 again.

Figure 14:
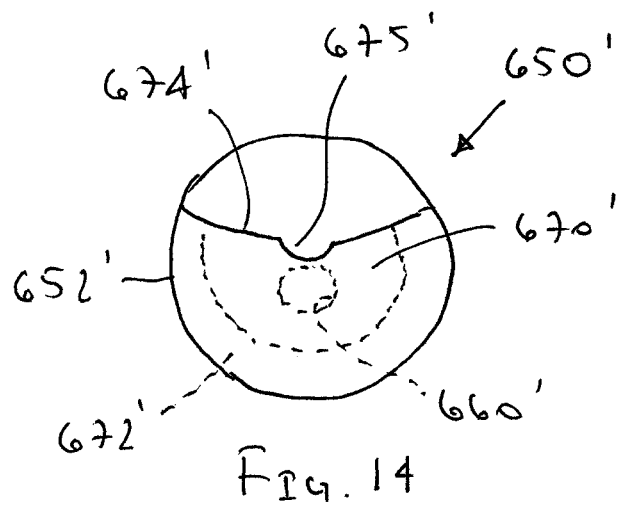
FIG. 14 is a front view of an alternative embodiment of the valve of FIGS. 10A and 10B including a release flap with a detent for guiding an instrument to access the passage.
Figure 15:
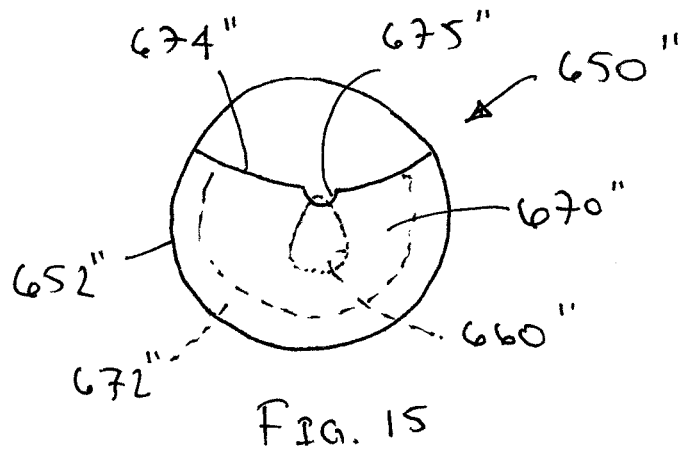
FIG. 15 is a front view of another alternative embodiment of the valve of FIGS. 10A and 10B including a passage having an eccentric shape and a release flap with a detent for guiding an instrument to access the passage.

Turning to FIG. 14, in an alternative embodiment, the open end 674' of the proximal flap 670' may include a recess or other feature that may facilitate guiding a tip of an instrument to push the flap 670' aside and enter the passage 660.' In addition or alternatively, the passage 660' may have different shapes, e.g., to facilitate introducing an instrument into the passage 660.' For example, FIG. 14 (and FIG. 10A) shows a passage 660' having a substantially circular cross-section. Alternatively, as shown in FIG. 15, the passage 660" may have a tear-drop or other eccentric shape, which may facilitate introducing an instrument into the passage 660." In addition or alternatively, if desired, the flap 670" may be attached only partially around a periphery of the central body region 652." For example, as shown in FIG. 15, the flap 670"may be attached around two thirds or three quarters around the periphery of the central body region 652." Alternatively, the flap 670" may be attached around about only half or less than half of the periphery, e.g., generally opposite the open end 674."

Figure 16:
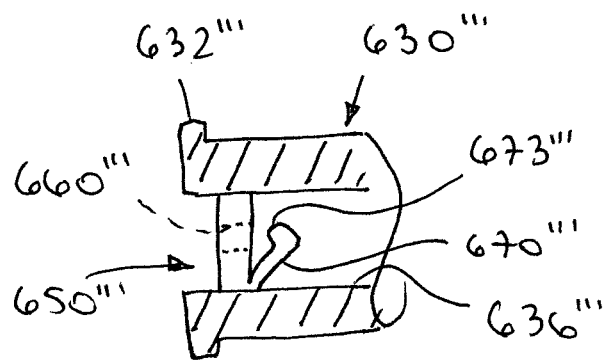
FIG. 16 is a cross-sectional detail of a hub showing yet another alternative embodiment of the valve of FIGS. 10A and 10B including a single flap having a detent that may be received in the passage when the flap seals the passage.

As shown in FIG. 16, if only a single release flap 670''' is provided on a valve 650,''' the valve 650''' may be attached to a hub 630''' such that the flap 670''' is located distally from a first end 632''' of the hub 630.''' Thus, an instrument introduced through the valve 650''' may freely enter the passage 660''' and then push the distal flap 670''' out of the way to accommodate the instrument being advanced into the lumen 636.''' If the instrument is removed, the distal flap 670''' may resiliently return to substantially seal the passage 660.'''

Optionally, in any of these embodiments, the flap(s) may include a tab or other feature that may be extend at least partially into the passage when the flap seals the passage. For example, FIG. 16 shows a flap 670''' including a raised tab 673''' that may be received in or otherwise engage the passage 670,''' e.g., to prevent undesired migration of the flap 670''' before an instrument is introduced into the valve 650''' and/or to enhance the seal.

In addition or alternatively, if desired in any of these embodiment, the passage may have a tapered or other shape, e.g., a funnel opening on the proximal end (not shown), which may facilitate guiding an instrument into the passage.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A hub for a sheath, catheter, or other tubular device, comprising:
    a tubular body comprising a first end, a second end, and a lumen extending therebetween and surrounding a central longitudinal axis, the lumen having a first cross-sectional area sized for receiving a medical device therethrough; and
    a valve secured within the lumen, the valve comprising an elastomeric valve body including front and rear surfaces extending across the lumen and a passage extending through the valve body between the front and rear surfaces and offset from the central axis, the valve body defining a second cross-sectional area larger than the first cross-sectional area in a relaxed state, the passage defining an oval shape in the relaxed state, the valve secured within the lumen in a compressed state in which the passage is biased to a closed configuration for substantially sealing the passage from fluid flow therethrough, the passage resiliently expandable to accommodate receiving an instrument therethrough while providing a substantially fluid tight seal around the instrument,
    wherein the valve body comprises a radial protrusion located radially from the passage relative to the central axis that imposes a radially inward force on the passage in the compressed state for biasing the passage to the closed configuration.

2. The hub of claim 1, wherein the tubular body comprises a kidney shape comprising a concave wall region opposite a convex wall region, and wherein the valve is secured within the lumen such that the passage is disposed between the central axis and the concave wall region.

3. The hub of claim 2, wherein the concave wall region comprises a relatively thin or weakened region that extends axially between the first and second ends of the tubular body for accommodating receiving a slitter tool for slitting the hub between the first and second ends.

4. The hub of claim 1, wherein the tubular body comprises a substantially circular cross-section, and wherein the valve body comprises an eccentric shape in the relaxed state, the valve body secured within the lumen in the compressed state that imposes a radially inward force on the valve body for biasing the passage to the closed configuration.

5. The hub of claim 4, wherein the valve body comprises an elliptical shape in the relaxed state, the valve body compressed to the compressed state having a cross-sectional area similar to the first cross-sectional area when the valve is secured within the lumen.

6. The hub of claim 1, wherein the valve is secured to the tubular body by at least one of an interference fit, an adhesive, one or more cooperating connectors, and a fused seam.

7. The hub of claim 1, wherein the passage comprises a relatively large region adjacent a relatively narrow region in the relaxed state, the relatively large region being subjected to lower compressive force in the compressed state such that the relatively large region opens before the relatively narrow region to accommodate instruments therethrough without expanding the relatively narrow region.

8. A hub for a sheath, catheter, or other tubular device, comprising:

a tubular body comprising a first end, a second end, and a substantially circular lumen extending therebetween and surrounding a central longitudinal axis, the lumen having a first cross-sectional area sized for receiving a medical device therethrough; and a valve secured within the lumen, the valve comprising a resilient valve body having a noncircular shape in a relaxed state defining a second cross-sectional area larger than the first cross-sectional area, the valve body comprising front and rear surfaces extending across the lumen, and a passage extending through the valve body between the front and rear surfaces and offset from the central axis, the valve secured within the lumen in a compressed state in which the passage is compressed to a closed configuration for substantially sealing the passage from fluid flow therethrough, the passage resiliently expandable to accommodate receiving an instrument therethrough while providing a substantially fluid tight seal around the instrument, wherein a radial protrusion extends radially from the valve body adjacent the passage for applying a radially compressive force to the passage in the compressed state to bias the passage to the closed configuration.

9. The hub of claim 8, wherein the valve body comprises an elliptical shape in the relaxed state.

10. The hub of claim 8, wherein the valve is secured to the tubular body by at least one of an interference fit, an adhesive, one or more cooperating connectors, and a fused seam.

11. The hub of claim 8, wherein the passage comprises a relatively large region adjacent a relatively narrow region in the relaxed state, the relatively large region being subjected to lower compressive force in the compressed state such that the relatively large region opens before the relatively narrow region to accommodate instruments therethrough without expanding the relatively narrow region.

12. The hub of claim 11, wherein the relatively larger region is disposed at one end of a major axis of the passage.

13. The hub of claim 8, wherein the passage defines an open shape in the relaxed state and is compressed to the closed configuration in the compressed state.

14. A hub for a sheath, catheter, or other tubular device, comprising:

a tubular body comprising a first end, a second end, and a lumen extending therebetween and surrounding a central longitudinal axis, the lumen having a first cross-sectional area sized for receiving a medical device therethrough; and a valve secured within the lumen, the valve comprising an elastomeric valve body including front and rear surfaces extending across the lumen and a passage extending through the valve body between the front and rear surfaces, the valve body defining a second cross-sectional area larger than the first cross-sectional area in a relaxed state, the valve secured within the lumen in a compressed state in which the passage is biased to a closed configuration for substantially sealing the passage from fluid flow therethrough, the passage resiliently expandable to accommodate receiving an instrument therethrough while providing a substantially fluid tight seal around the instrument, wherein the valve body comprises a radial protrusion located radially from the passage relative to the central axis that imposes a radially inward force on the passage in the compressed state for biasing the passage to the closed configuration.

15. The hub of claim 14, wherein the tubular body comprises a substantially circular cross-section, and wherein the valve body comprises an eccentric shape in the relaxed state, the valve body secured within the lumen in the compressed state.

16. The hub of claim 14, wherein the valve body comprises an elliptical shape in the relaxed state, the valve body compressed to the compressed state having a cross-sectional area similar to the first cross-sectional area when the valve is secured within the lumen.

17. The hub of claim 14, wherein the passage defines an open shape in the relaxed state and is compressed to the closed configuration in the compressed state.

18. The hub of claim 14, wherein the valve is secured to the tubular body by at least one of an interference fit, an adhesive, one or more cooperating connectors, and a fused seam.

19. The hub of claim 14, wherein the passage comprises a relatively large region adjacent a relatively narrow region in the relaxed state, the relatively large region being subjected to lower compressive force in the compressed state such that the relatively large region opens before the relatively narrow region to accommodate instruments therethrough without expanding the relatively narrow region.

20. The hub of claim 19, wherein the relatively larger region is disposed at one end of the major axis of the passage.

* * * * *